(12) United States Patent
Johnston

(10) Patent No.: US 9,149,480 B2
(45) Date of Patent: Oct. 6, 2015

(54) USE OF MELOXICAM FOR THE LONG-TERM TREATMENT OF MUSCULOSKELETAL DISORDERS IN CATS

(75) Inventor: Laura Johnston, Ingelheim am Rhein (DE)

(73) Assignee: Boehringer Ingeleheim Vetmedica GmbH, Ingeleheim am Rhein (DE)

( * ) Notice: Subject to any disclaimer, the term of this patent is extended or adjusted under 35 U.S.C. 154(b) by 0 days.

(21) Appl. No.: 13/581,661

(22) PCT Filed: Mar. 3, 2010

(86) PCT No.: PCT/EP2010/052728
§ 371 (c)(1),
(2), (4) Date: Oct. 19, 2012

(87) PCT Pub. No.: WO2011/107150
PCT Pub. Date: Sep. 9, 2011

(65) Prior Publication Data
US 2013/0035330 A1    Feb. 7, 2013

(51) Int. Cl.
*A61K 31/5415*    (2006.01)

(52) U.S. Cl.
CPC .................................. *A61K 31/5415* (2013.01)

(58) Field of Classification Search
CPC ................................................. A61K 31/5415
See application file for complete search history.

(56) References Cited

U.S. PATENT DOCUMENTS

| | | |
|---|---|---|
| 2,795,529 A | 6/1957 | Album et al. |
| 3,288,675 A | 11/1966 | Newmark et al. |
| 3,849,549 A | 11/1974 | Dempski et al. |
| 3,931,212 A | 1/1976 | Satzinger et al. |
| 3,947,576 A | 3/1976 | Kuczkowski et al. |
| 4,233,299 A | 11/1980 | Trummlitz et al. |
| 4,482,554 A | 11/1984 | Gebhardt et al. |
| 4,543,200 A | 9/1985 | Sherman |
| 4,628,053 A | 12/1986 | Fries |
| 4,748,174 A | 5/1988 | Veronesi |
| 4,794,117 A | 12/1988 | Corbiere |
| 4,802,926 A | 2/1989 | Kussendrager et al. |
| 4,835,187 A | 5/1989 | Reuter et al. |
| 4,942,167 A | 7/1990 | Chiesi et al. |
| 5,169,847 A | 12/1992 | Nagy nee Kricsfalussy et al. |
| 5,283,065 A | 2/1994 | Doyon et al. |
| 5,304,561 A | 4/1994 | Sarfarazi |
| 5,360,611 A | 11/1994 | Robertson et al. |
| 5,380,934 A | 1/1995 | Inoue et al. |
| 5,414,011 A | 5/1995 | Fu et al. |
| 5,599,535 A | 2/1997 | Polansky et al. |
| 5,654,003 A | 8/1997 | Fuisz et al. |
| 5,674,888 A | 10/1997 | Polansky et al. |
| 5,700,816 A | 12/1997 | Isakson et al. |
| 5,811,446 A | 9/1998 | Thomas |
| 5,824,658 A | 10/1998 | Falk et al. |
| 5,886,030 A | 3/1999 | Maniar |
| 5,962,012 A | 10/1999 | Lin et al. |
| 6,046,191 A | 4/2000 | Hamley et al. |
| 6,071,539 A | 6/2000 | Robinson et al. |
| 6,090,800 A | 7/2000 | Unger et al. |
| 6,106,862 A | 8/2000 | Chen et al. |
| 6,136,804 A | 10/2000 | Nichtberger |
| 6,156,349 A | 12/2000 | Steinbach et al. |
| 6,166,012 A | 12/2000 | Muller et al. |
| 6,180,136 B1 | 1/2001 | Larson et al. |
| 6,183,779 B1 | 2/2001 | Ouali et al. |
| 6,184,220 B1 | 2/2001 | Turck et al. |
| 6,187,800 B1 | 2/2001 | Suri et al. |
| 6,221,377 B1 | 4/2001 | Meyer |
| 6,284,269 B1 | 9/2001 | Struengmann et al. |
| 6,319,519 B2 | 11/2001 | Woolfe et al. |
| 6,495,603 B1 | 12/2002 | Miyake et al. |
| 6,550,955 B2 | 4/2003 | D'Silva |
| 6,599,529 B1 | 7/2003 | Skinhøj et al. |
| 6,605,295 B1 | 8/2003 | Bellmann et al. |
| 6,630,056 B1 | 10/2003 | Thibierge et al. |
| 6,669,957 B1 | 12/2003 | Laruelle et al. |
| 6,682,747 B1 | 1/2004 | Turck et al. |
| 6,869,948 B1 | 3/2005 | Bock et al. |
| 6,986,346 B2 | 1/2006 | Hochrainer et al. |
| 7,105,512 B2 | 9/2006 | Morizono et al. |
| 7,969,206 B2 | 6/2011 | Ito |
| 2001/0055569 A1 | 12/2001 | Davis et al. |
| 2002/0006440 A1 | 1/2002 | Cherukuri |
| 2002/0016342 A1 | 2/2002 | Scolnick et al. |
| 2002/0035107 A1 | 3/2002 | Henke et al. |
| 2002/0068088 A1 | 6/2002 | Gruber |
| 2002/0077328 A1 | 6/2002 | Hassan et al. |
| 2002/0099049 A1 | 7/2002 | Burch et al. |
| 2002/0106345 A1 | 8/2002 | Uhrich et al. |
| 2002/0187187 A1 | 12/2002 | Ohki et al. |
| 2003/0050305 A1 | 3/2003 | Tejada |
| 2003/0055051 A1 | 3/2003 | Morizono et al. |
| 2003/0109701 A1 | 6/2003 | Coppi et al. |

(Continued)

FOREIGN PATENT DOCUMENTS

| | | |
|---|---|---|
| AU | 673675 B2 | 11/1996 |
| AU | 762464 B2 | 6/2003 |

(Continued)

OTHER PUBLICATIONS

Merriam Webster webpage; treatment definition; http://www.merriam-webster.com/dictionary/treatment,accessed Dec. 19, 2013.*

(Continued)

*Primary Examiner* — Timothy Thomas

(74) *Attorney, Agent, or Firm* — Michael P. Morris; Joyce L. Morrison

(57) ABSTRACT

The invention is directed to the use of a formulation comprising meloxicam or a pharmacologically acceptable meloxicam salt of an organic or inorganic base thereof for the long-term treatment of musculoskeletal disorders in cats. No negative effects on renal function occur following a treatment from 10 to 20 months or more.

7 Claims, No Drawings

(56) References Cited

U.S. PATENT DOCUMENTS

| | | |
|---|---|---|
| 2003/0119825 A1 | 6/2003 | Folger et al. |
| 2003/0199482 A1 | 10/2003 | Seibert et al. |
| 2003/0220306 A1 | 11/2003 | Simmons et al. |
| 2003/0235589 A1 | 12/2003 | Demopulos et al. |
| 2004/0001883 A1 | 1/2004 | Matsui et al. |
| 2004/0024041 A1 | 2/2004 | Selzer |
| 2004/0024042 A1 | 2/2004 | Breyer |
| 2004/0037869 A1 | 2/2004 | Cleverly et al. |
| 2004/0043992 A1 | 3/2004 | Tolba et al. |
| 2004/0110747 A1 | 6/2004 | Altman |
| 2004/0171611 A1 | 9/2004 | Trummlitz et al. |
| 2004/0180092 A1 | 9/2004 | Henke et al. |
| 2004/0198826 A1 | 10/2004 | Baiker et al. |
| 2004/0204413 A1 | 10/2004 | Faour et al. |
| 2004/0204472 A1 | 10/2004 | Briggs et al. |
| 2004/0214753 A1 | 10/2004 | Britten et al. |
| 2004/0229038 A1 | 11/2004 | Cooper et al. |
| 2004/0234596 A1 | 11/2004 | Ohki et al. |
| 2004/0253312 A1 | 12/2004 | Sowden et al. |
| 2005/0038018 A1 | 2/2005 | Kanbe et al. |
| 2005/0147664 A1 | 7/2005 | Liversidge et al. |
| 2005/0187212 A1 | 8/2005 | Ohki et al. |
| 2005/0187213 A1 | 8/2005 | Lang et al. |
| 2005/0197332 A1 | 9/2005 | Altman |
| 2005/0244491 A1 | 11/2005 | Ohki et al. |
| 2005/0245510 A1 | 11/2005 | Friton et al. |
| 2005/0277634 A1 | 12/2005 | Janott et al. |
| 2005/0288280 A1 | 12/2005 | Friton et al. |
| 2006/0079516 A1 | 4/2006 | Henke et al. |
| 2006/0160793 A1 | 7/2006 | Altman |
| 2006/0217431 A1 | 9/2006 | Daemmgen et al. |
| 2007/0077296 A1 | 4/2007 | Folger et al. |
| 2007/0099907 A1 | 5/2007 | Altman |
| 2007/0193894 A1 | 8/2007 | Macken et al. |
| 2007/0249727 A1 | 10/2007 | Martin et al. |
| 2008/0132493 A1 | 6/2008 | Folger et al. |
| 2008/0234380 A1 | 9/2008 | Shapiro |
| 2008/0280840 A1 | 11/2008 | Lang et al. |
| 2011/0083985 A1 | 4/2011 | Folger et al. |
| 2011/0275618 A1 | 11/2011 | Folger et al. |
| 2012/0077764 A1 | 3/2012 | Freehauf et al. |
| 2013/0178467 A1 | 7/2013 | Henke et al. |
| 2014/0066440 A1 | 3/2014 | Folger et al. |
| 2014/0113893 A1 | 4/2014 | Folger et al. |

FOREIGN PATENT DOCUMENTS

| | | |
|---|---|---|
| CA | 1102802 | 6/1981 |
| CA | 2164100 A1 | 1/1995 |
| CA | 2166204 A1 | 1/1995 |
| CA | 2264626 A1 | 3/1998 |
| CA | 2326517 A1 | 10/1999 |
| CA | 2404360 A1 | 9/2001 |
| CA | 2414063 A1 | 12/2001 |
| CA | 2469588 | 6/2003 |
| CA | 2503396 A1 | 5/2004 |
| DE | 3434707 A1 | 4/1985 |
| DE | 3700172 A1 | 7/1987 |
| DE | 4217971 C1 | 10/1993 |
| DE | 19729879 A1 | 1/1999 |
| DE | 10010123 A1 | 9/2001 |
| DE | 10024752 A1 | 11/2001 |
| DE | 10032132 A1 | 1/2002 |
| DE | 10300323 A1 | 10/2004 |
| EP | 0002482 A1 | 6/1979 |
| EP | 0034432 A2 | 8/1981 |
| EP | 0093999 A2 | 11/1983 |
| EP | 0177870 A2 | 4/1986 |
| EP | 0179430 A2 | 4/1986 |
| EP | 0306984 A1 | 3/1989 |
| EP | 0360246 A1 | 3/1990 |
| EP | 0390071 A1 | 10/1990 |
| EP | 0422681 A1 | 4/1991 |
| EP | 0465235 A1 | 1/1992 |
| EP | 0560329 A1 | 9/1993 |
| EP | 0945134 A1 | 9/1999 |
| EP | 1082966 | 3/2001 |
| EP | 1190714 A2 | 3/2002 |
| EP | 1568369 A1 | 8/2005 |
| ES | 2065846 A1 | 2/1995 |
| ES | 2159564 T3 | 10/2001 |
| FR | 2437838 A1 | 4/1980 |
| GB | 2455875 A | 6/2009 |
| IT | 1251650 B | 5/1995 |
| JP | 47007352 Y1 | 3/1972 |
| JP | 1299230 | 12/1989 |
| JP | 11139971 A | 5/1999 |
| JP | 2001170083 A | 6/2001 |
| JP | 2003535902 A | 12/2003 |
| JP | 3550782 B2 | 8/2004 |
| JP | 4018022 B2 | 12/2007 |
| JP | 04321624 B2 | 8/2009 |
| WO | 9301814 A1 | 2/1993 |
| WO | 9400420 A1 | 1/1994 |
| WO | 9509639 A1 | 4/1995 |
| WO | 9517178 A1 | 6/1995 |
| WO | 9518604 A1 | 7/1995 |
| WO | 9603387 A1 | 2/1996 |
| WO | 9603388 A1 | 2/1996 |
| WO | 9610999 A2 | 4/1996 |
| WO | 9611192 A1 | 4/1996 |
| WO | 9640102 A1 | 12/1996 |
| WO | 9640103 A1 | 12/1996 |
| WO | 9641625 A1 | 12/1996 |
| WO | 9703655 A1 | 2/1997 |
| WO | 9703667 A1 | 2/1997 |
| WO | 9717978 A1 | 5/1997 |
| WO | 9717989 A1 | 5/1997 |
| WO | 9729776 A1 | 8/1997 |
| WO | 9731631 A1 | 9/1997 |
| WO | 9809654 A1 | 3/1998 |
| WO | 9817250 A1 | 4/1998 |
| WO | 9909988 A1 | 3/1999 |
| WO | 9912524 A1 | 3/1999 |
| WO | 9927906 A1 | 6/1999 |
| WO | 9949845 A1 | 10/1999 |
| WO | 9949867 A1 | 10/1999 |
| WO | 9959634 A1 | 11/1999 |
| WO | 0015195 A1 | 3/2000 |
| WO | 0108689 A1 | 2/2001 |
| WO | 0137838 A1 | 5/2001 |
| WO | 0152897 A2 | 7/2001 |
| WO | 0187343 A2 | 11/2001 |
| WO | 0197813 A2 | 12/2001 |
| WO | 02085331 A1 | 10/2002 |
| WO | 03049733 A2 | 6/2003 |
| WO | 03082297 A1 | 10/2003 |
| WO | 03097066 A1 | 11/2003 |
| WO | 2004004776 A1 | 1/2004 |
| WO | 2004026116 A2 | 4/2004 |
| WO | 2004026313 A1 | 4/2004 |
| WO | 2004037264 A1 | 5/2004 |
| WO | 2004089379 A2 | 10/2004 |
| WO | 2004103283 A2 | 12/2004 |
| WO | 2005002542 A2 | 1/2005 |
| WO | 2005004915 A2 | 1/2005 |
| WO | 2005079806 A1 | 9/2005 |
| WO | 2005105101 | 11/2005 |
| WO | 2005115386 A1 | 12/2005 |
| WO | 2006000306 A1 | 1/2006 |
| WO | 2006100213 A1 | 9/2006 |
| WO | 2007039417 A1 | 4/2007 |
| WO | 2007087214 A1 | 8/2007 |
| WO | 2007135505 A2 | 11/2007 |
| WO | 2008113149 A2 | 9/2008 |
| WO | 2008152122 A2 | 12/2008 |
| WO | 2009049304 A1 | 4/2009 |
| WO | 2011046853 A1 | 4/2011 |
| WO | 2011107150 A1 | 9/2011 |
| WO | 2011107498 A1 | 9/2011 |
| WO | 2011138197 A2 | 11/2011 |

(56) References Cited

OTHER PUBLICATIONS

Lane; "Confidence Interval on the Mean"; http://onlinestatbook.com/2/estimation/mean.html; accessed Jun. 12, 2014.*
Abstract in English of JP2001170083, 2001.
Abstract in English of JP4018022, 2007.
Abstract in English of JP3550782, 2004.
Abstract in English of WO9301814, 1993.
Chemical Abstracts, vol. 118, No. 18, Abstract No. 175803, XP002087682, 1993, 1 page.
Abstract in English of ES2065846, 1995.
Gerritsen et al., "Prostaglandin Synthesis and Release from Cultured Human Trabecular-meshwork Cells and Scleral Fibroblasts". Experimental Eye Research, vol. 43, No. 6, 1986, pp. 1089-1102.
Herbort et al., "Anti-inflammatory Effect of Topical Diclofenac After Argon Laser Trabeculoplasty: Preliminary Results of a Placebo Controlled Study". Klin. Monatsbl. Augenheik, vol. 200, No. 5, May 1992, pp. 358-361.
Pharma Projects, Dialog File 928, Accession Nr. 0021312, Diclofenac, InSite Vision, 1996, 5 pages.
Snyder et al., "Corticosteroid Treatment and Trabecular Meshwork Proteases in Cell and Organ Culture Supernatants". Experimental Eye Research, vol. 57, No. 4, 1993, pp. 461-468.
Masferrer et al., "Cyclooxygenase-2 Inhibitors: A New Approach to the Therapy of Ocular Inflammation". Survey of Ophthalmology, vol. 41, Supp. 2, Feb. 1997, pp. S35-S40.
Abstract in English for IT1251650, 1995.
Li et al., "Degradation mechanism and kinetic studies of a novel anticancer agent, AG2034". International Journal of Pharmaceutics, vol. 167, 1998, pp. 49-56.
Bunji, Kouho, "Tissue Damage Due to Infections". Drug Injection Handbook, Fundamentals of Blending Variation for Injection Drugs, Nanzando Co. Ltd., Tokyo, 1976, p. 5.
Pharmaceutical Excipent Encyclopedia, Yakuji Nippo Ltd., Tokyo, 1994, pp. 2-5.
"Committee for Veterinary Medicinal Products-Meloxicam (Extension to PIGS)—Summary Report (5)". The European Agency for the Evaluation of Medicinal Products, Veterinary Medicines and Information Technology, Dec. 2000, pp. 1-3.
"Metacam (R) 0.5 mg/ml oral suspension for cats." Boehringer Ingelheim Datasheet, Web site: http://www.vetgb.com/vetgb_pdfs/metacamc_7a5c_vetgb.pdf> Accessed on Jun. 8, 2010.
"Metacam Professional Insert: Metacam® (meloxicam) 1.5 mg/mL Oral Suspension (equivalent to 0.05 mg per drop) Non-Steroidal anti-inflammatory drug for oral use in dogs only". Boehringer Ingelheim, Jan. 2005, 2 pages.
"Metacam(R)"FDA Animal & Veterinary Drug Labels, WEB site: http://www.fda.gov/downloads/AnimalVeterinary/Products/ApprovedAnimalDrugProducts/DrugLabels/UCM050397.pdf> Accessed Jun. 8, 2010.
"Metacam—Community register of veterinary medicinal products" accessed online at http://pharmacos.eudra.org/F2/register/v004.htm.
"Types of Solutions". University of Wisconsin, Stevens Point, Feb. 1, 2001, accessed at http://www.uwsp.edu/chemistry/tzamis/chem106pdfs/solutionexamples.pdf, Google date sheet included, 2 pages.
Abstract in English of DE10024752, 2001.
Abstract in English of DE3434707, 1985.
Abstract in English of FR2437838, 1980.
Abstract in English of JP02906528, 1999.
Abstract in English of JP11139971, 1999.
Abstract in English of JP47007352, 1972.
Altman et al., "Efficacy Assessment of Meloxicam, a Preferential Cyclooxygenase-2 Inhibitor, in Acute Coronary Syndromes Without ST-Segment Elevation: The Nonsteroidal Anti-Inflammatory Drugs in Unstable Angina Treatment-2 (NUT-2) Pilot Study". Circulation, vol. 106, 2002, pp. 191-195.
Ansel et al., "Pharmaceutical Dosage Forms and Drug Delivery Systems". Seventh Edition, Lippincott Williams & Wilkins, Philadelphia, PA, 1999, pp. 77-87.
Clarke et al., "Feline osteoarthritis: a prospective study of 28 cases". Journal of Small Animal Practice, vol. 47, 2006, pp. 439-445.
Del Tacca et al., "Efficacy and Tolerability of Meloxicam, a COX-2 Preferential Nonsteroidal Anti-Inflammatory Drug". Clinical Drug Investigation, vol. 22, No. 12, 2002, pp. 799-818.
Engelhardt et al., "Meloxicam: Influence on Arachidonic Acid Metabolism". Biochemical Pharmacology, vol. 51, 1996, pp. 21-28.
Ettmayer et al., "Lessons Learned from Marketed and Investigational Prodrugs". Journal of Medicinal Chemistry, vol. 47, No. 10, May 2004, pp. 2393-2404.
European Search Report for EP10155400 dated Jun. 9, 2010.
European Search Report for EP10162015 dated Aug. 30, 2010.
Fitzgerald et al., "COX-2 inhibitors and the cardiovascular system". Clinical and Experimental Rheumatology, vol. 19, No. 6, Supp. 25, Nov. 2001, pp. S31-S36.
Giuliani et al., "Role of Antithrombotic Therapy in Cardiac Disease". Mayo Clinic Practice of Cardiology, Third Edition, Mosby, St. Louis, MO, 1996, pp. 1116-1121.
Gollackner et al., "Increased apoptosis of hepatocyctes in vascular occulusion after orthotopic liver transplantation". Transplant International, vol. 13, No. 1, 2000, pp. 49-53.
Gunew et al., "Long-term safety, efficacy and palatability of oral meloxicam at 0.01-0.03 mg/kg for treatment of osteoarthritic pain in cats". Journal of Feline Medicine and Surgery, vol. 10, 2008, pp. 235-241.
Hawkey et al., "Gastrointestinal Tolerability of Meloxicam Compared to Diclofenac in Osteoarthritis Patients". British Journal of Rheumatology, vol. 37, No. 9, 1998, pp. 937-945.
International Search Report and Written Opinion for PCT/EP2010/052728 mailed Jul. 1, 2010.
Kumar et al., "Comparative Studies on Effect of Some Hydrophilic Polymers on the Dissolution Rate of a Poorly Water Soluble Drug, Meloxicam". Indian Drugs, vol. 39, No. 6, Apr. 2002, pp. 323-329.
Lieberman et al., "Tablet Formulation and Design" in Pharmaceutical Dosage Forms: Tablets, vol. 1, Second Edition, Marcel Dekker, Inc., New York, New York, 1989, pp. 105-108.
Luger et al., "Structure and physicochemical properties of meloxicam, a new NSAID". European Journal of Pharmaceutical Sciences, vol. 5, 1996, pp. 175-187.
Noble et al., "Meloxicam". Drugs, vol. 51, No. 3, Mar. 1996, pp. 424-430.
Physicians' Desk Reference, 55th Edition, Medical Economics Company, Inc., 2001, pp. 981-984 and pp. 1404-1406.
Remington: The Science and Practice of Pharmacy, 19th Edition, vol. II, Mack Publishing Company, Easton, Pennsylvania, 1995, p. 1646.
Robson et al., "Intrinsic acute renal failure (ARF) associated with non-steroidal anti-inflammatory drug (NSAId) use in juvenile cats undergoing routine desexing-16 cases 1998-2005". May 2006, Journal of Veterinary Internal Medicine, vol. 20, No. 3, Abst. 109, p. 740.
Rudnic et al., "Oral Solid Dosage Forms"., Gennaro, Editior, Remington's Pharmaceutical Sciences, 18th Edition, Mack Publishing Company, Easton, PA, 1990, pp. 1633-1645 and pp. 1654-1655.
Saha et al., "Effect of solubilizing excipients on permeation of poorly water-soluble compounds across Caco-2 cell monolayers". European Journal of Pharmaceutics and Biopharmaceutics, vol. 50, No. 3, 2000, pp. 403-411, Abstract accessed at http://cat.inist.fr/?aModele=afficheN&cpsidt=798854, accessed on Aug. 13, 2010, 3 pages.
Stei et al., "Local Tissue Tolerability of Meloxicam, a New NSAID: Indications for Parental, Dermal and Mucosal Administration". British Journal of Rheumatology, vol. 35, Supp. 1, 1996, pp. 44-50.
Tuerck et al., "Clinical Pharmacokinetics of Meloxicam". Arzneimittel-Forschung, vol. 47, No. 3, 1997, pp. 253-258.
Vippagunta et al., "Crystalline solids". Advanced Drug Delivery Reviews, vol. 48, 2001, pp. 3-26.
Nell et al., "Comparison of vedaprofen and meloxicam in dogs with muskuloskeletal pain and inflammation". Journal of Small Animal Practice, vol. 43, No. 5, May 2002, pp. 208-212 [Accessed at http://www.ncbi.nlm.nih.gov/pubmed/12038853 on Sep. 27, 2013]. Abstract Only, 1 page.

(56) References Cited

OTHER PUBLICATIONS

"Meloxicam Veterinary—Systemic"., The United States Pharmacopeial Convention, 2004, pp. 1-9. [Accessed at http://vetmed.tamu.edu/common/docs/public/aavpt/meloxicam.pdf on Aug. 16, 2013].

"Staging System for Chronic Kidney Disease"., IRIS: International Renal Interest Society, 2006, pp. 1-4.

Bednarek et al., "Effect of steroidal and non-steroidal anti-imflammatory drugs in combination with long-acting oxytetracycline on non-specific immunity of calves suffering from enzootic bronchopneumonia". Veterinary Microbiology, vol. 96, 2003, pp. 53-67.

Bednarek et al., "The effect of steroidal and non-steroidal anti-inflammatory drugs on the cellular immunity of calves with experimentally-induced local lung inflammation". Veterinary Immunology and Immunopathology, vol. 71, 1999, pp. 1-15.

Boehringer Ingelheim; Metacam (Meloxicam) Now Approved for Pigs and Mastitis in Dairy Cows; May 2003 Press Release; pp. 1-2.

Cho et al., "In vitro effects of Actinobacillus pleuropneumoniae on inducible nitric oxide synthase and cyclooxygenase-2 in porcine alveolar macrophages". American Journal of Veterinary Research, vol. 64, No. 12, Dec. 2003, pp. 1514-1518.

D'Yakov et al., "Long term use of Tamsulosin (omnic®) in Patients with Chronic Prostatitis". Urologiia, vol. 5, 2002, pp. 10-12.

Dellabella et al., "Conservative Managment of Juxtavesical Calculi with Tamsulosin". European Urology Supplements, vol. 2, No. 1, 2003, p. 81.

DOW Chemicals Brochure, entitled "Using Methocel cellulose ethers for controlled release of drugs in hyrophilic matrix systems." Publication Jul. 2000, Form No. 198-02075-700 AMS, pp. 1-36.

Dunn et al., "Tamsulosin: A Review of its Pharmacology and Therapeutic Efficacy in the Management of Lower Urinary Tract Symptoms". Drugs & Aging, vol. 19, No. 2, 2002, pp. 132-161.

Farkouh et al., "Comparison of lumiracoxib with naproxen and ibuprofen in the Therapeutic Arthritis Research and Gastrointestinal Event Trial (TARGET), cardiovascular outcomes: randomised controlled trial". Lancet, vol. 364, Aug. 2004, pp. 675-684.

Fiedorczyk, D.M., "Renial Failure in Cats". Misericordia University, Internet Archive Date: Sep. 7, 2006, http://www.misericordia.edu/honorus/dfpaper.cfm [Retrieved on Dec. 12, 2012].

Fitzpatrick et al., "Recognising and Controlling Pain and Inflammation in Mastitis". Proceedings of the British Mastitis Conference, Axient/Institute for Animal Health, Milk Development Council/Novartis Animal Health, 1998, pp. 36-44.

Gowan, R., "Retrospective Analysis of Long-Term Use of Meloxicam in Aged Cats with Musculoskeletal Disorders and the Effect of Renal Function". Journal of Veterinary Internal Medicine, vol. 23, Abstract No. 87, 2009, p. 1347.

Gruet et al., "Bovine mastitis and intramammary drug delivery: review and perspectives". Advanced Drug Delivery Reviews, vol. 50, 2001, pp. 245-259.

Guth et al., "Pharmacokinetics and pharmacodynamics of terbogrel, a combined thromboxane A2 receptor and synthase inhibitor, in healthy subjects". British Journal of Clinical Pharmacology, vol. 58, No. 1, Jul. 2004, pp. 40-51.

Hirsch et al, "Investigation on the efficacy of meloxicam in sows with mastitis-metritis-agalactia syndrome". Journal of Veterinary Pharmacology and Therapeutics, vol. 26, 2003, pp. 355-360.

Hydrated Silica Webpage; http://science.kosmix.com/topic/hydrated_silica; Kosmix Corporation, Apr. 21, 2011, pp. 1-14.

Jain et al., "Antiplatelet therapy in acute coronary syndromes without persistent ST-segment elevation". Cardiovascular Drugs and Therapy, vol. 15, No. 5, Sep. 2001, pp. 423-436. [Abstract Only].

Kimura et al., "Effect of cilostazol on platelet agrregation and experimental thrombosis". Arzneimittel-Forschung, vol. 35, No. 7A, 1985, pp. 1144-1149. [Abstract Only].

Macdonald Campus of McGill University, "Mastitis in Dairy Cows", published online, Jul. 2003, pp. 1-12.

McDonald et al., "Calpain inhibitor I reduces the activation of nuclear factor-KappaB and Organ Injury/Dysfunction in Hemorrhagic Shock". The FASEB Journal, vol. 15, Jan. 2001, pp. 171-186.

Parikh et al., Binders and Solvents, Chapter 4, Handbook of Pharmaceutical Granulation Technology, First Edition, Marcel Dekker, 1997, pp. 59-67.

Rantanen et al., "Process Analysis of Fluidized Bed Granulation". AAPS PharmsciTech, vol. 2, No. 4, Article 21, 2001, 8 pages.

Schneeweis et al., "In Vivo and In Vitro Diclofenac Sodium Evaluation After Rectal Application of Soft Gelatine Capsules Enabling Application Induced Transformation (AIT) into a Seminsolid System of Liquid Crystals (SSLC) for Controlled Release". Pharmaceutical Research, vol. 14, No. 12, Dec. 1997, pp. 1726-1729.

Sciencelab.com, "Lactose, Monohydrate, Spray-Dried Powder, NF". Accessed at http://www.epoxy-paint.net/page/.S/PVAR/10419/SLL1453, Feb. 29, 2008, 2 pages.

Straus et al., "New Evidence for Stroke Prevention: Clinical Applications". The Journal of the American Medical Association, vol. 288, No. 11, Sep. 2002, pp. 1396-1398.

Straus et al., "New Evidence for Stroke Prevention: Scientific Review". The Journal of the American Medical Association, vol. 288, No. 11, Sep. 2002, pp. 1388-1395.

Sunose et al., "The Effect of Cyclooxygenase 2 Inhibitor, FK3311, on Ischemia-Reperfusion Injury in Canine Lung Transplantation". Journal of Heart and Lung Transplantation, vol. 19, No. 1, Jan. 2000, p. 40.

Tunuguntla et al., "Management of Prostatitis". Prostate Cancer and Prostatic Diseases, vol. 5, No. 3, 2002, pp. 172-179.

Wagenlehner et al., "Therapy of Prostatitis Syndrome". Der Urologe [A], vol. 40, No. 1, 2001, pp. 24-28. [English Abstract at p. 25].

Lascelles et al., "Nonsteroidal anti-inflammatory drugs in cats: a review". Veterinary Annesthesia and Analgesia, 2007, pp. 1-23.

\* cited by examiner

US 9,149,480 B2

USE OF MELOXICAM FOR THE LONG-TERM TREATMENT OF MUSCULOSKELETAL DISORDERS IN CATS

FIELD OF THE INVENTION

The present invention is directed to the long-term use of meloxicam to treat musculoskeletal disorders in cats with and without pre-existing renal disease without any negative effects on renal function.

BACKGROUND OF THE INVENTION

Meloxicam is the only molecule licensed for treatment of chronic musculoskeletal disorders in cats. These conditions affect the quality of life of cats and often require treatment. Impaired renal function is currently listed as a contraindication on NSAID data sheets. However, chronic renal disease and chronic musculoskeletal disorders, such as osteoarthritis (OA) are common in elderly cats and often coexist. Osteoarthritis affects synovial joints, associated with loss of cartilage, inflammation, bone remodelling and formation of osteophytes. It is usually idiopathic and primarily affects elbow joints and hips. Clinical signs include for example difficulty in jumping, lameness, stiffness as well as behavioural changes such as demeanour, reduced grooming and resentment of handling.

Meloxicam was licensed for long-term use in cats in 2007 at an oral dose of 0.1 mg/kg on day 1 followed by 0.05 mg/kg. However, there is no prior art that demonstrates that the use of meloxicam is appropriate for long-term treatment of feline. It is reported by Gunew that feline suffering from osteoarthritis can be treated with meloxicam in a concentration range between 0.01-0.03 mg/kg. (Gunew et al., Long-term safety, efficacy and palatability of oral meloxicam at 0.01-0.03 mg/kg for treatment of osteoarthritic pain in cats. Journal of Feline Medicine and Surgery 2008, 10, 235-241) The trials were completed after a mean treatment duration of 5.8 months. However, since this study does not include any comparable placebo product and uses subjective measurements only, its conclusions are questionable. A short-term (23 days) concept study performed by Clarke & Bennett has also shown that a daily meloxicam dosage of 0.05 mg/cat can be used to treat osteoarthritis. (Clarke & Bennett, Feline osterarthritis: a prospective study of 28 cases. Journal of Small Animal Practice 2006, 47, 439-445) This study does not include any thorough investigation and assessment of meloxicam treatment over a longer period of time.

Therefore, it is an object of the present invention to develop a long-term treatment of musculoskeletal disorders in cats, especially aged cats, with and without pre-existing renal disease and without accelerating the progression of renal diseases in cats.

DESCRIPTION OF THE INVENTION

Surprisingly, it has been found that meloxicam or a pharmacologically acceptable meloxicam salt of an organic or inorganic base thereof may be used for the long-term treatment of musculoskeletal disorders in cats, especially aged cats, with or without pre-existing renal disease, without having any negative effect on renal functions in cats during a treatment from 10 to 40 months or more.

Thus, the invention related to the use of meloxicam or a pharmacologically acceptable meloxicam salt of an organic or inorganic base thereof for the preparation of a veterinary medical composition having analgesic efficacy for the long-term treatment of musculoskeletal disorders such as but not limiting to osteoarthritis in cats, particularly in older cats, without having any negative effects on renal functions during a treatment from 10 to 40 months or more. Treatment with such a formulation will not accelerate already existing renal diseases in older cats, nor initiate any renal disease. According to the invention the pharmacologically acceptable meloxicam salt comprises the meglumine, potassium or ammonium salt, preferably the meloxicam meglumine salt.

The present invention provides a formulation containing meloxicam or a pharmacologically acceptable meloxicam salt of an organic or inorganic base, one or more vehicles, and optionally one or more suitable additives, for the long term treatment of musculoskeletal disorders in cats, characterised in that no negative effects on renal function occur during a treatment from 10 to 40 months or more. Further the invention relates to the use of a formulation containing meloxicam or a pharmacologically acceptable meloxicam salt of an organic or inorganic base and one or more vehicles for preparing a veterinary medical composition having analgesic efficacy for the long-term treatment of musculoskeletal disorders in cats, characterised in that no negative effects on renal function occur during a treatment from 10 to 40 months or more. Said formulation contains or essentially consists of meloxicam or a pharmacologically acceptable salt thereof, water, optionally one or more additives selected from group of consisting of buffers, solubilisers, preservatives and optionally thickeners.

Meloxicam or a pharmacologically acceptable salt thereof for the long-term treatment of musculoskeletal disorders in cats having a pre-existing renal disease or having no pre-existing renal disease. Further, the invention relates to meloxicam or a pharmacologically acceptable salt thereof for the long-term treatment of musculoskeletal disorders in cats with chronic kidney disease. The musculoskeletal disease comprises but not limited to osteoarthritis.

The treatment occurs over a long-term period of at least 6 months, preferred ranges are selected from the group selected of 10 to 40 months, 10 to 37 months, 10 to 30 months, 10 to 25 months, 10 to 20 months, 10 to 17 months, 11 to 40 months, 11 to 37 months, 11 to 30 months, 11 to 25 months, 11 to 20 months, 11 to 17 months, 12 to 40 months, 12 to 37 months, 12 to 30 months, 12 to 25 months, 12 to 20 months, 12 to 17 months, 13 to 40 months, 13 to 37 months, 13 to 30 months, 13 to 25 months, 13 to 20 months, 13 to 17 months, 14 to 40 months, 14 to 37 months, 14 to 30 months, 14 to 25 months, 14 to 20 months and 14 to 17 months.

Older cats or aged cats are herein defined as being 5 years old or older, preferably from 5 to 20 years, even more preferably from 7 to 17 years, especially preferred from 10 to 13.4 to 15.5 to 16 years. Studies have shown that 53% of cats over 7 years of age have renal diseases. Renal diseases may include acquired renal diseases such as chronic tubulo-interstitial nephritis, glomerulonephritis, pyelonephritis, amyloidosis, hydronephrosis, renal lymphoma or congenital diseases that cause kidney failure in cats such as polycystic kidney disease, renal aplasia, renal hypoplasia, renal dysplasia, amyloidosis. These may or may not be in a chronic disease state. However, the treatment is also appropriate for cats over 5 years of age without any pre-existing renal diseases.

In another embodiment the treatment of cats may be performed in a formulation useful for cats that are 5 years or older. The daily dose of the formulation is between 0.01 and 0.075 mg/kg daily, preferably 0.05 mg/kg. The lowest effective dose for a median maintenance dose was found to be 0.02 mg/kg. This range can be used to treat musculoskeletal disease such as osteoarthritis. The musculoskeletal disease is a chronic disease. The formulation contains or essentially consists of meloxicam salt, water, optionally one or more additives selected from the group consisting of buffers, solubilisers, preservatives and optionally thickeners.

EXAMPLE

The medical records of a feline-only practice were searched for cats with OA being treated with meloxicam during a 4 year period. A diagnosis of OA was based upon any two of the following: owner noted mobility changes and/or physical examination findings or radiographic changes. Cats included were older than 7 years and treated with meloxicam for a duration of more than 6 months. Complete medical records were available for review. Biochemistry, urinalysis and body weight were regularly monitored. The progression of renal disease in the aged non-renal and renal group treated was compared to age matched and IRIS matched untreated controls from the same clinic.

These results prove that a maintenance dose of 0.02 mg/kg meloxicam does not hasten progression of renal disease in aged cats or aged cats with pre-existent stable IRIS stage 1-3 renal disease. Therefore meloxicam can be used as a treatment for aged cats with painful musculoskeletal disorders and concurrent renal disease. The aged cats treated with NSAID therapy shall be carefully monitored.

MATERIALS AND METHODS

The database of a feline-only practice in suburban Melbourne was searched for cats which had been treated for chronic musculoskeletal disorders with meloxicam (Metacam oral suspension, Boehringer Ingelheim) during a 4 year period. The diagnosis of osteoarthritis or spondylosis deformans had been made based upon any two of the following: owner noted mobility changes, physical examination findings or radiographic changes. The inclusion criteria included cats greater than 7 years old which had been treated continuously with meloxicam for a duration of more than 6 months and which had complete medical records available for review. In addition, cats were only included if serum biochemistry, urine analysis and body weight had been regularly monitored.

Young cats were excluded, as were cats with no pre-treatment renal parameter measurements. In addition cats were also excluded if the owner could not be contacted to check that the cats were still receiving daily treatment with meloxicam.

Age, breed, sex, concomitant diseases and medications as well as date treatment commenced, treatment duration and daily dose of meloxicam were recorded.

The presence or absence of pre-treatment renal disease and staging of the renal disease was carried out using plasma creatinine and urine specific gravity according to the following recognised International Renal Interest Society criteria (IRIS staging 2006):

www.iris-kidney.com

IRIS stage 1: Inadequate concentrating ability, abnormal renal palpation. Creatinine<140 µmol/l (<1.6 mg/dL)

IRIS stage 2: Mild or absent clinical signs associated with renal disease. Creatinine 140-250 µmol/l (1.6-2.8 mg/dL)

IRIS stage 3: Many clinical signs present. Creatinine 251-440 µmol/l (2.8-5 mg/dL)

The treated cats were then subdivided into two groups: the renal treated group that belonged to IRIS stage 1-3 and were pre-treated, and the non-renal treated group that has no identifiable renal disease pre-treatment. Urine specific gravity, serum creatinine and bodyweight were used as indicators of renal disease progression. The progression of renal disease was then compared to age and IRIS matched untreated controls were then randomly identified from the database of the same clinic.

STATISTICAL ANALYSIS

The median age of the renal and non-renal treated cats, median treatment duration and median maintenance dose was calculated.

The progression of renal disease in the non-renal treated group was compared to the age matched untreated controls. The progression of renal disease in the treated renal-diseased group was compared to age matched and IRIS matched untreated controls from the same clinic. Statistical analysis was carried out using a time adjusted area-under-the-curve (AUC) changes from baseline time 0 until the last recorded value (n).

$$AUC_{(0-n),adj} = \frac{AUC_{(0-n)}}{t_n - t_0} = \frac{\sum_{i=0}^{n} \frac{C_i + C_{i+1}}{2}(t_{i+1} - t_i)}{t_n - t_0}$$

$t_0$: time point of first measurement (baseline)
$t_n$: time point of last measurement
$C_i$: difference of parameter concentration at time point $i=0, \ldots, n$ to baseline The Wilcoxon rank-sum-test was used to compare the groups. With this nonparametric test the distribution of the adjusted AUC of two groups was compared regarding the location. Under the null hypothesis it is assumed that there is no location shift in the distributions of the two treatment groups. If the resulting p-value is lower than the two-sided significance level of 5% the null hypothesis is rejected.

Results

Out of a total database of 3016 cats, 214 cats which had been treated with Metacam® oral suspension were identified. Of these, 38 cats met the inclusion criteria for the treated group. 22 cats of these cats (58%) had IRIS stage 1-3 renal disease prior to treatment, whereof 8 cats were categorized to fit IRIS stage 1, 13 cats belonged to stage 2 and 1 cat was classified to belong to stage 3. 16 cats had no identifiable renal disease prior to treatment.

The median age of the renal treated group was 15.5 years and the non-renal treated group was 13.4 years.

The median treatment duration was 527 days in the renal group and 400 days in the non-renal group. After dose titration to the lowest effective dose, the median maintenance dose was 0.02 mg/kg daily in both the renal treated and non-renal treated groups. There were no differences in the progression of renal parameters in the renal group treated with meloxicam versus the age and IRIS matched untreated renal group or the non-renal group treated with meloxicam versus the non-renal group not treated with meloxicam.

Two renal-treated cats were excluded from analysis of creatinine changes from baseline as their pre-treatment sample was not carried out within 3 days of the start of treatment. There were no statistically significant differences in weight loss or the loss of urine concentrating ability in the renal group treated with meloxicam versus the age and IRIS matched untreated renal group or the non-renal group treated with meloxicam versus the non-renal group not treated with meloxicam. Mean serum creatinine concentration increased statistically significantly less over time in the renal group treated with meloxicam than in the renal untreated group.

EXAMPLE

The following formulation may be used according to the invention but not limited to:

1) Metacam® Suspension Boehringer Ingelheim for Cats

The invention claimed is:

1. A method for the long-term treatment of musculoskeletal disorders in cats comprising administering to a cat an effective daily dose of meloxicam or a pharmaceutically acceptable meloxicam salt of an organic or inorganic base thereof, wherein the daily dose is greater than 0.05 mg/kg and no greater than 0.075 mg/kg and no acceleration of any existing renal disease in the cat or no initiation of any renal disease in the cat occurs during a treatment at the daily dose for a period of 13 to 40 months.

2. A method according to claim 1, wherein the cat has a pre-existing renal disease.

3. A method according to claim 1, wherein the cat has no pre-existing renal disease.

4. A method according to claim 1, wherein the cat has a chronic kidney disease.

5. A method according to claim 1, wherein the daily dose is no greater than 0.06 mg/kg daily.

6. A method according to claim 1, wherein the musculoskeletal disease is osteoarthritis.

7. A method according to claim 1, wherein the musculoskeletal disease is a chronic disease.

* * * * *